US010252475B2

(12) United States Patent
Xu (10) Patent No.: US 10,252,475 B2
(45) Date of Patent: Apr. 9, 2019

(54) METHODS FOR ALIGNING FIBERS WITH AN ELECTRICAL FIELD AND COMPOSITE MATERIALS

(71) Applicant: Florida State University Research Foundation, Inc., Tallahassee, FL (US)

(72) Inventor: Chengying Xu, Tallahassee, FL (US)

(73) Assignee: Florida State University Research Foundation, Inc., Tallahassee, FL (US)

(*) Notice: Subject to any disclaimer, the term of this patent is extended or adjusted under 35 U.S.C. 154(b) by 198 days.

(21) Appl. No.: 15/287,027

(22) Filed: Oct. 6, 2016

(65) Prior Publication Data

US 2017/0095981 A1    Apr. 6, 2017

Related U.S. Application Data

(60) Provisional application No. 62/237,827, filed on Oct. 6, 2015.

(51) Int. Cl.

| | | |
|---|---|---|
| *G01N 27/447* | (2006.01) | |
| *B29C 70/14* | (2006.01) | |
| *B29C 35/08* | (2006.01) | |
| *B03C 5/00* | (2006.01) | |
| *B29K 63/00* | (2006.01) | |
| *B29K 105/14* | (2006.01) | |
| *B29K 307/04* | (2006.01) | |

(52) U.S. Cl.
CPC .............. *B29C 70/14* (2013.01); *B03C 5/005* (2013.01); *B29C 35/0805* (2013.01); *G01N 27/447* (2013.01); *G01N 27/44756* (2013.01); *B29C 2035/0827* (2013.01); *B29K 2063/00* (2013.01); *B29K 2105/14* (2013.01); *B29K 2307/04* (2013.01); *B29K 2995/0006* (2013.01)

(58) Field of Classification Search
CPC ........... G01N 27/447; G01N 27/44756; G01N 27/453; B03C 5/005–5/028
See application file for complete search history.

(56) References Cited

U.S. PATENT DOCUMENTS

| | | | | |
|---|---|---|---|---|
| 3,629,083 A | * | 12/1971 | Brendle | ................. B01J 19/087 204/165 |
| 4,707,231 A | | 11/1987 | Berger | |
| 5,057,253 A | | 10/1991 | Knoblach | |
| 5,196,212 A | | 3/1993 | Knoblach | |
| 5,580,512 A | * | 12/1996 | Koon | ...................... B29C 70/14 264/108 |

(Continued)

FOREIGN PATENT DOCUMENTS

SU            1014844 A   *   4/1983   ................ C08J 3/28

OTHER PUBLICATIONS

Rámon-Azcón et al., "Dielectrophoretically Aligned Carbon Nanotubes to Control Electrical and Mechanical Properties of Hydrogels to Fabricate Contractile Muscle Myofibers," Adv. Mater. 2013, 25, 4028-4034 (Year: 2013).*

(Continued)

*Primary Examiner* — Alexander S Noguerola
(74) *Attorney, Agent, or Firm* — Eversheds Sutherland (US) LLP (57) ABSTRACT

Methods of aligning fibers with an electric field are provided. The fibers may include dielectric fibers, such as carbon fibers. The fibers may be aligned in a liquid that is curable. Composite materials also are provided that include aligned fibers.

20 Claims, 3 Drawing Sheets

(56) References Cited

U.S. PATENT DOCUMENTS

| | | | |
|---|---|---|---|
| 5,846,356 A | 12/1998 | Vyakarnam et al. | |
| 5,888,340 A | 3/1999 | Vyakarnam et al. | |
| 6,025,285 A | 2/2000 | Vyakarnam et al. | |
| 8,915,377 B2 * | 12/2014 | Gandhi | B07B 1/00 209/315 |
| 2013/0341837 A1 * | 12/2013 | Gandhi | B29C 45/1701 264/437 |

OTHER PUBLICATIONS

Naseer et al., Surface acoustic waves induced micropatterning of cells in gelatin methacroyl (GelMA) hydrogels, 2017 Biofabrication 9 015020 (Year: 2017).*

Arguin et al., "Electric field induced alignment of multiwalled carbon nanotubes in polymers and multiscale composites," Advanced Manufacturing: Polymer & Composites Science, vol. 1, No. 1, Jan. 30, 2015 pp. 16-25 (Year: 2015).*

Derwent English langauge abstract of SU 1014844A, patent published Apr. 30, 1983. (Year: 1983).*

EPO computer-generated English langauge translation of SU 1014844A, patent published Apr. 30, 1983. (Year: 1983).*

Ladani et al., "Improving the toughness and electrical conductivity of epoxy nanocomposites by using aligned carbon nanofibers," Composites Science and Technology, 117 (2015) 146-158, available online Jun. 18, 2015 (Year: 2015).*

Cheng et al., "High mechanical performance composite conductor: Multi-Walled Carbon Nanotube Sheet/Bismaleimide Nanocomposites", Advanced Functional Materials, 2009, 19, pp. 3219-3225.

Hedberg, et al., "Air flow technique for large scale dispersion and alignment of carbon nanotubes on various substrates", Applied Physics Letters, 2005, 86, 143111.

Steinert, et al., "Magnetic field alignment and electrical properties of solution cast PET-carbon nanotube composite films", Polymer, 2009, 50 (3), pp. 898-904.

Sulong. et al., "Alignment of multi-walled carbon nanotubes in a polyethylene matrix by extrusion shear flow: mechanical properties enhancement", Journal of Composite Materials , 2010, 45 (8), pp. 931-941.

Tian, et al., "The fabrication of single-walled carbon nanotube/polyelectrolyte multilayer composites by layer-by-layer assembly and magnetic field assisted alignment", Nanotechnology, 2009, 20, 335601.

Wang, et al., "Highly oriented carbon nanotube papers made of aligned carbon nanotubes", Nanotechnology, 2008, 19, 075609, pp. 1-6.

Xin, et al., "Directional orientation of carbon nanotubes on surfaces using a gas flow cell", Nano Letters 2004, 4 (8) 1481-1484.

* cited by examiner

METHODS FOR ALIGNING FIBERS WITH AN ELECTRICAL FIELD AND COMPOSITE MATERIALS

CROSS-REFERENCE TO RELATED APPLICATIONS

This application claims priority to U.S. Provisional Patent Application No. 62/237,827, filed Oct. 6, 2015, which is incorporated herein by reference.

BACKGROUND

In the relevant literature, there are multiple ways to align fibers, especially carbon nanotubes (CNTs), such as by magnetic field (see, e.g., Tian Y. et al. Nanotechnology 20, 335601 (2009); and Steinert, B. W. et al. Polymer 50, 898 (2009)), gas flow (see, e.g., Xin H. et al. Nano Letters 4, 1481 (2004); and Hedberg, J. et al. Applied Physics Letters 86, 143111 (2005)), shear flow of polymer matrix (see, e.g., Abu Bakar S. et al. Journal of Composite Materials 45, 931 (2010)), mechanical shear press (see, e.g., Wang D. et al. Nanotechnology 19, 075609 (2008)), and mechanical stretch alignment (see, e.g., Cheng, Q. et al. Advanced Functional Materials 19, 3219 (2009)). These techniques, however, typically require high cost, are complex, and/or restrict the possible sizes of the samples containing the fibers.

For example, the use of mechanical forces to align CNTs or carbon nanofibers (CNFs) can permit the alignment of large samples, but typically requires the CNTs to have specific characteristics and/or involves a complicated process. Mechanical processing also can cause damage to the fibers' microstructure, thereby reducing mechanical strength. The use of a mechanical force also can make it difficult to realize a mat or tissue shaped fiber preform.

Also, the use of magnetic forces typically is costly and not environmentally friendly, because obtaining sufficient magnetic forces to align fibers usually requires an intense field to magnetize the fibers to micro-magnets, which consumes relatively large amounts of energy and increases processing costs.

Therefore, improved alignment methods that do not rely on magnetic and/or mechanical forces to align fibers are desirable. Also desired are alignment methods that lessen the risk of damaging the fibers, that do not consume relatively large amounts of energy, and/or that permit the alignment of fibers in relatively large samples.

BRIEF SUMMARY

Provided herein are methods of aligning fibers. In embodiments, the methods comprise providing one or more fibers of a dielectric material disposed in a liquid; and exposing the one or more fibers to an electric field for a time sufficient to at least substantially align at least a portion of the fibers. The one or more fibers may comprise carbon fibers, CNFs, CNTs, Si, $SiO_2$, SiC, $Si_3N_4$, $Al_2O_3$, or a combination thereof.

Also provided herein are composite materials comprising one or more fibers of a dielectric material aligned by the methods provided herein.

DETAILED DESCRIPTION

Provided herein are methods of alignment that can be performed, in certain embodiments, within a relatively short amount of time and/or with a relatively weak electric field. The electric field may use less energy than other methods of alignment, provides the possibility of employing a relatively simple apparatus, and/or does not produce by-products during processing. For at least these reasons, embodiments of the methods provided herein are environmentally friendly.

In embodiments, the methods comprise providing one or more fibers in a liquid, and exposing the fibers to an electric field to at least partially align at least a portion of the fibers. In one embodiment, providing one or more fibers in a liquid comprises disposing one or more fibers in the liquid. The one or more fibers may be disposed in the liquid before, during, or after the liquid is exposed to an electric field. The liquid and the one or more fibers may be combined by any means known in the art, and the liquid and one or more fibers may be stirred, sonicated, and/or heated.

The one or more fibers may be dispersed in the liquid. In one embodiment, the fibers are substantially evenly dispersed in the liquid. The formation of a dispersion of fibers in the liquid may be assisted by any means, including, but not limited to, stirring, sonication, and/or heating. The weight percentage of fibers in the liquid, in embodiments, is about 0.1 to about 20 weight %, based on the total weight of the liquid and fibers. The weight percentage of fibers in the liquid, in some embodiments, is about 0.1 to about 15 weight %, based on the total weight of the liquid and fibers. The weight percentage of fibers in the liquid, in additional embodiments, is about 0.1 to about 10 weight %, based on the total weight of the liquid and fibers. The weight percentage of fibers in the liquid, in further embodiments, is about 0.1 to about 5 weight %, based on the total weight of the liquid and fibers. The weight percentage of fibers in the liquid, in still further embodiments, is about 0.1 to about 1 weight %, based on the total weight of the liquid and fibers.

The electric field may be provided by any means known in the art. In one embodiment, the electric field is provided by two electrodes connected to a power supply. The two electrodes may be metal electrodes, such as a copper electrodes and/or zinc electrodes. The fibers and liquid may be arranged between the two electrodes. The two electrodes may be spaced any distance apart as long as they are capable of imparting a desired electric field. In embodiments, the distance between the electrodes is about 1 mm to about 10 mm. In further embodiments, the distance between the electrodes is about 1 mm to about 8 mm. In still further embodiments, the distance between the electrodes is about 1 mm to about 6 mm. In additional embodiments, the distance between the electrodes is about 1 mm to about 4 mm. In some embodiments, the distance between the electrodes is about 1 mm to about 3 mm. In a particular embodiment, the distance between the electrodes is about 2 mm.

The two electrodes may be arranged adjacent to a fabricating tank in which the liquid and one or more fibers are disposed. The fabricating tank may have a first side and a second side, and the two electrodes may flank the fabricating tank, i.e., one electrode is arranged on the first side of the fabricating tank, and the second electrode is arranged on the second side of the fabricating tank. The fabricating tank and the two electrodes may be adhered to each other by tape, glue, or other means. The fabricating tank also may be associated with a UV lamp, a heat source, or both a heat source and a UV lamp. The dimensions of the fabricating tank may be adjusted to provide a composite material of a desired shape and/or size.

Figure 1:
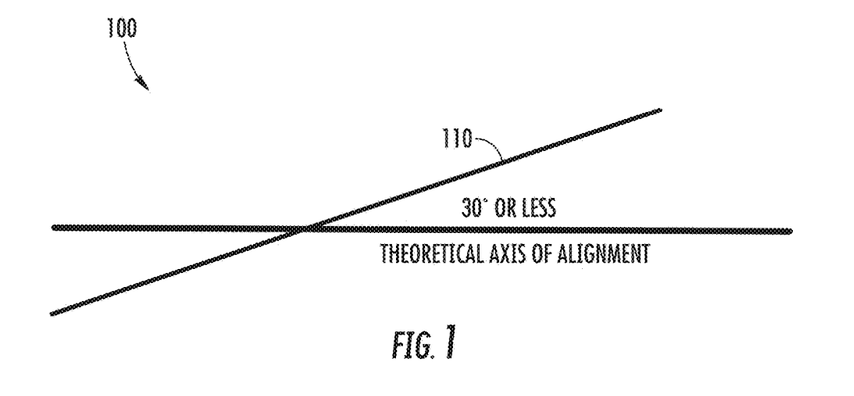
FIG. 1 is a schematic depicting one embodiment of a discontinuous fiber at least substantially aligned with a theoretical axis of alignment.

In one embodiment, at least a portion of the fibers is substantially aligned by an electric field. In another embodiment, substantially all of the fibers are substantially aligned by an electric field. As used herein, the phrase "substantially aligned" refers to at least a portion of fibers of which a majority of the fibers is positioned so that the angle between at least a part of each fiber of the majority and the theoretical axis of alignment is 30° or less, as shown at FIG. 1. FIG. 1 is a schematic 100 that includes a fiber 110 that is substantially aligned with the theoretical axis of alignment. The "theoretical axis of alignment" is determined by the position each of the one or more fibers is expected to assume upon sufficient exposure to an electric field.

In embodiments, the weakest electric field capable of substantially aligning at least a portion of the fibers is used. In other embodiments, the electric field used to align at least a portion of the fibers exceeds the theoretical weakest electric field by about 0.1 to about 1%, about 0.1 to about 5%, about 0.1 to about 10%, about 0.1 to about 15%, about 0.1 to about 20%, or about 0.1 to about 25%. An estimation of polarizability tensor may be employed to facilitate the calculation of the weakest electric field (see, e.g., Example 2). Not wishing to be bound by any particular theory, it is believed that a number of parameters can affect the minimum electric field intensity required to at least substantially align at least a portion of a particular sample of fibers. These parameters can include, but are not limited to, [1] the average length of the fibers, [2] the average diameter of the fibers, [3] the dielectric constant of the fibers, [4] the dielectric constant of the liquid, [5] the fabrication temperature, and/or [6] the viscosity of the liquid. Not wishing to be bound by any particular theory, it is believed the weakest electric field capable of substantially aligning at least a portion of the fibers decreases in intensity as [1] the length of the fibers increases, [2] the diameter of the fibers increases, and/or [3] the fabrication temperature decreases. Not wishing to be bound by any particular theory, it is believed that the viscosity of the liquid does not substantially affect the required electric field, but a smaller viscosity can shorten the time required to at least substantially align at least a portion of the fibers. Lastly, not wishing to be bound by any particular theory, it is believed that the dielectric constants of the fibers and liquid has a combined effect: the larger the $K_1(K_2-K_1)^2/(K_2+2K_1)^2$, the smaller the weakest electric field capable of substantially aligning at least a portion of the fibers.

In embodiments, the electric field applied by the electrodes is about 20 V/mm to about 60 V/mm. In further embodiments, the electric field applied by the electrodes is about 30 V/mm to about 50 V/mm. In some embodiments, the electric field applied by the electrodes is about 40 to V/mm about 50 V/mm. In embodiments, the electric field is about 46.6 V/mm. In embodiments, the power provided by the power source is about 75 V to about 125 V.

In other embodiments, the power provided by the power source is about 90 V to about 110 V. In still further embodiments, the power provided by the power source is about 93.2 V.

In embodiments, the electric field applied by the electrodes is about 20 V/mm to about 60 V/mm, and the power provided by the power source is about 75 V to about 125 V. In further embodiments, the electric field applied by the electrodes is about 30 V/mm to about 50 V/mm, and the power provided by the power source is about 90 V to about 110 V. In some embodiments, the electric field applied by the electrodes is about 40 V/mm to about 50 V/mm, and the power provided by the power source is about 90 V to about 110 V. In embodiments, the electric field is about 46.6 V/mm, and the power provided by the power source is about 93.2 V.

In embodiments, at least a portion of the fibers is at least substantially aligned upon being exposed to an electric field for about 1 second to about 20 minutes. In some embodiments, at least a portion of the fibers is at least substantially aligned upon being exposed to an electric field for about 10 seconds to about 20 minutes. In particular embodiments, at least a portion of the fibers is at least substantially aligned upon being exposed to an electric field for about 15 seconds to about 20 minutes. In further embodiments, at least a portion of the fibers is at least substantially aligned upon being exposed to an electric field for about 1 minute to about 20 minutes. In still further embodiments, at least a portion of the fibers is at least substantially aligned upon being exposed to an electric field for about 1 minute to about 15 minutes. In one embodiment, at least a portion of the fibers is at least substantially aligned upon being exposed to an electric field for about 15 seconds. In particular embodiments, the one or more fibers and the liquid is exposed to an electric field for a time sufficient to impart a desired degree of alignment.

As the fibers align or after the fibers align, a concatenation phenomenon might occur, which may or may not be desirable, depending on the desired properties of the one or more fibers or the materials comprising the one or more fibers. As used herein, the phrase "concatenation phenomenon" refers to the tendency of two fibers to link to and/or contact each other at their ends. In one embodiment, exposure of the one or more fibers to an electric field is ceased after at least a portion of the one or more fibers is substantially aligned or after a desired degree of alignment is achieved, thereby preventing or minimizing the concatenation phenomenon. In another embodiment, exposure of the one or more fibers to an electric field is continued after at least a portion of the one or more fibers is substantially aligned or after a desired degree of alignment is achieved, thereby promoting or maximizing the concatenation phenomenon. Not wishing to be bound by any particular theory, it is believed that the concatenation phenomenon can be controlled by optimizing the processing time, i.e., exposure of the one or more fibers to the electric field, adjusting the viscosity of the liquid, and/or adjusting the volume fraction of the one or more fibers in the liquid. For example, it is believed that increasing the viscosity of the liquid, and increasing the volume fraction of the one or more fibers in the liquid may prevent or minimize the concatenation phenomenon.

In embodiments, the methods comprise curing the liquid in which the fibers are disposed. Curing may be performed while the one or more fibers are exposed to an electric field and/or after the one or more fibers have been exposed to an electric field for any desired time. Curing may be achieved by any means known in the art, and may include polymerization, cross-linking, or both polymerization and cross-linking. Curing may be assisted by a UV lamp and/or heat source, which may be associated with a fabricating tank, as described herein.

Fibers

In embodiments, the one or more fibers aligned by the methods provided herein are fibers of one or more dielectric materials. Examples of dielectric materials include carbon, Si, $SiO_2$, SiC, $Si_3N_4$, $Al_2O_3$, etc.

The one or more fibers may be discontinuous fibers. The discontinuous fibers may be chopped fibers.

The one or more fibers, in some embodiments, comprise carbon. The one or more fibers, in particular embodiments, comprise carbon fibers, CNTs, CNFs, or a combination thereof. The CNTs may be single wall carbon nanotubes (SWCNTs), multi-wall carbon nanotubes (MWCNTs), or a combination thereof.

At least a portion of the one or more fibers may be functionalized with one or more functional groups. For example, the one or more functional groups may include a functional group, such as an epoxide, capable of reacting with a non-solvent liquid, such as an epoxy resin. As a further example, the one or more functional groups may include a functional group that is responsive to an electric field, thereby assisting the alignment of the fibers, and/or facilitating the achievement of a desired degree of alignment.

The fibers, including the carbon fibers, may be nanoscale fibers, i.e., fibers having an average length of about 1 nm to about 500 nm, microscale fibers, i.e., fibers having an average length of about 1 µm to about 500 µm, macroscale fibers, i.e., fibers having an average length of about 1 mm to about 100 mm, or a combination thereof. The average lengths and average diameters of the fibers may be determined by an optical microscope or scanning electron microscopy, depending on whether the size of the fibers permits the use of an optical microscope.

In embodiments, the fibers have an average length of about 1 µm to about 200 µm. In particular embodiments, the fibers have an average length of about 2 µm to about 200 µm. In other embodiments, the fibers have an average length of about 125 µm to about 175 µm. In one embodiment, the fibers have an average length of about 2 µm. In another embodiment, the fibers have an average length of about 10 µm. In yet another embodiment, the fibers have an average length of about 100 µm. In some embodiments, the fibers have an average length of about 150 µm.

In embodiments, the fibers have an average length of about 1 mm to about 100 mm. In particular embodiments, the fibers have an average length of about 1 mm to about 50 mm. In some embodiments, the fibers have an average length of about 10 mm to about 50 mm.

In embodiments, the fibers have an average diameter of about 0.1 µm to about 14 µm. In further embodiments, the fibers have an average diameter of about 0.1 µm to about 11 µm. In particular embodiments, the fibers have an average diameter of about 0.1 µm to about 8 µm. In some embodiments, the fibers have an average diameter of about 1 µm to about 8 µm. In one embodiment, the fibers have an average diameter of about 0.1 µm. In another embodiment, the fibers have an average diameter of about 1 µm. In a particular embodiment, the fibers have an average diameter of about 8 µm.

In embodiments, the fibers have an average length of about 1 µm to about 200 µm, and an average diameter of about 0.1 µm to about 14 µm. In other embodiments, the fibers have an average length of about 125 µm to about 175 µm, and an average diameter of about 0.1 µm to about 11 µm. In some embodiments, the fibers have an average length of about 150 µm, and an average diameter of about 8 µm.

In embodiments, the fibers have an average length of about 1 mm to about 100 mm, and an average diameter of about 0.1 µm to about 14 µm. In other embodiments, the fibers have an average length of about 1 mm to about 50 mm, and an average diameter of about 0.1 µm to about 11 µm.

In embodiments, the fibers have an average length of about 1.5 µm to about 2.5 µm, and an average diameter of about 0.1 µm to about 1 µm. In further embodiments, the fibers have an average length of about 1.5 µm to about 2.5 µm, and an average diameter of about 0.1 µm. In particular embodiments, the fibers have an average length of about 1.5 µm to about 2.5 µm, and an average diameter of about 1 µm. In some embodiments, the fibers have an average length of about 2.0 µm, and an average diameter of about 0.1 µm to about 1 µm. In certain embodiments, the fibers have an average length of about 2.0 µm, and an average diameter of about 0.1 µm. In still further embodiments, the fibers have an average length of about 2.0 µm, and an average diameter of about 1 µm.

Liquid

The liquid, in embodiments, is at least one non-solvent. The term "non-solvent", as used herein, refers to a liquid in which the one or more fibers are at least substantially insoluble.

The liquid may be a polymer precursor, such as a resin. The resin may be an epoxy resin. The polymer precursor, including the epoxy resin, may cure upon exposure to UV light, heat, or a combination thereof. The liquid may be an epoxy resin, including a low viscosity liquid epoxy resin, a bismaleimide, a polyureasilazane precursor, or a combination thereof.

The liquid may include one or more additives. For example, the liquid may include one or more additives that reduces or increases the viscosity of the liquid. As a further example, the liquid may include one or more additives, such as a flame retardant, that imparts one or more desirable properties to the liquid and/or the resulting composite material.

Composite Materials

Composite materials also are provided herein. The composite materials, in embodiments, comprise one or more fibers aligned by the methods provided herein.

Not wishing to be bound by any particular theory, it is believed that by at least substantially aligning discontinuous fibers, in certain embodiments, according to the methods provided herein, composite materials having desired structural and/or functional properties can be produced.

The composite materials generally may be of any size and/or shape. The size and/or shape may be determined, at least in part, by the dimensions of a fabricating tank. In one embodiment, the composite material is mat-shaped or tissue-shaped. Other shapes are possible, however, including bulk composite materials.

In one embodiment, the composite material is a mat-shaped material having dimensions of about 12 inches by about 12 inches by about 2 mm, the fibers have an average length of about 2 μm and an average diameter of about 0.1 μm to about 1 μm, and the electric field (V) used to align the fibers is about $1.143 \times 10^5$ to about $2.248 \times 10^5$ at a fabrication temperature of about 10 K, about $3.408 \times 10^6$ to about $6.701 \times 10^6$ at a fabrication temperature of about 298.15 K, about $4.265 \times 10^6$ to about $8.388 \times 10^6$ at a fabrication temperature of about 373.15 K, and about $5.408 \times 10^6$ to about $1.064 \times 10^7$ at a fabrication temperature of about 473.15 K. The fibers of this embodiment may comprise carbon fibers, CNFs, CNTs, or a combination thereof.

In one embodiment, the composite material is a mat-shaped material having dimensions of about 12 inches by about 12 inches by about 2 mm, the fibers have an average length of about 10 μm and an average diameter of about 0.1 μm to about 1 μm, and the electric field (V) used to align the fibers is about $1.946 \times 10^4$ to about $2.032 \times 10^4$ at a fabrication temperature of about 10 K, about $5.802 \times 10^5$ to about $6.058 \times 10^5$ at a fabrication temperature of about 298.15 K, about $7.261 \times 10^5$ to about $7.582 \times 10^5$ at a fabrication temperature of about 373.15 K, and about $9.207 \times 10^5$ to about $9.614 \times 10^5$ at a fabrication temperature of about 473.15 K. The fibers of this embodiment may comprise carbon fibers, CNFs, CNTs, or a combination thereof.

In one embodiment, the composite material is a mat-shaped material having dimensions of about 12 inches by about 12 inches by about 2 mm, the fibers have an average length of about 100 μm and an average diameter of about 0.1 μm to about 1 μm, and the electric field (V) used to align the fibers is about $6.430 \times 10^2$ at a fabrication temperature of about 10 K, about $1.916 \times 10^4$ to about $1.917 \times 10^4$ at a fabrication temperature of about 298.15 K, about $2.399 \times 10^4$ at a fabrication temperature of about 373.15 K, and about $3.042 \times 10^4$ at a fabrication temperature of about 473.15 K. The fibers of this embodiment may comprise carbon fibers, CNFs, CNTs, or a combination thereof.

In one embodiment, the composite material is a mat-shaped material having dimensions of about 12 inches by about 12 inches by about 2 mm, the fibers have an average length of about 1 mm and an average diameter of about 0.1 μm to about 1 μm, and the electric field (V) used to align the fibers is about 20.329 at a fabrication temperature of about 10 K, about 606.102 to about 606.105 at a fabrication temperature of about 298.15 K, about 758.577 at a fabrication temperature of about 373.15 K, and about 961.867 at a fabrication temperature of about 473.15 K. The fibers of this embodiment may comprise carbon fibers, CNFs, CNTs, or a combination thereof.

In one embodiment, the composite material is a mat-shaped material having dimensions of about 12 inches by about 12 inches by about 2 mm, the fibers have an average length of about 10 mm and an average diameter of about 0.1 μm to about 1 μm, and the electric field (V) used to align the fibers is about 0.643 at a fabrication temperature of about 10 K, about 19.167 at a fabrication temperature of about 298.15 K, about 23.994 at a fabrication temperature of about 373.15 K, and about 30.424 at a fabrication temperature of about 473.15 K. The fibers of this embodiment may comprise carbon fibers, CNFs, CNTs, or a combination thereof.

In one embodiment, the composite material is a mat-shaped material having dimensions of about 12 inches by about 12 inches by about 2 mm, the fibers have an average length of about 50 mm and an average diameter of about 0.1 μm to about 1 μm, and the electric field (V) used to align the fibers is about 0.058 at a fabrication temperature of about 10 K, about 1.714 at a fabrication temperature of about 298.15 K, about 2.164 at a fabrication temperature of about 373.15 K, and about 2.744 at a fabrication temperature of about 473.15 K. The fibers of this embodiment may comprise CNFs, CNTs, or a combination thereof. The fibers of this embodiment may comprise carbon fibers, CNFs, CNTs, or a combination thereof.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1—Alignment of Fibers

In this example, chopped carbon fibers were aligned in an electric field. Chopped carbon fibers were chosen for this example, because the size of carbon nanofibers did not permit them to be clearly observed with an optical microscope.

Figure 2:
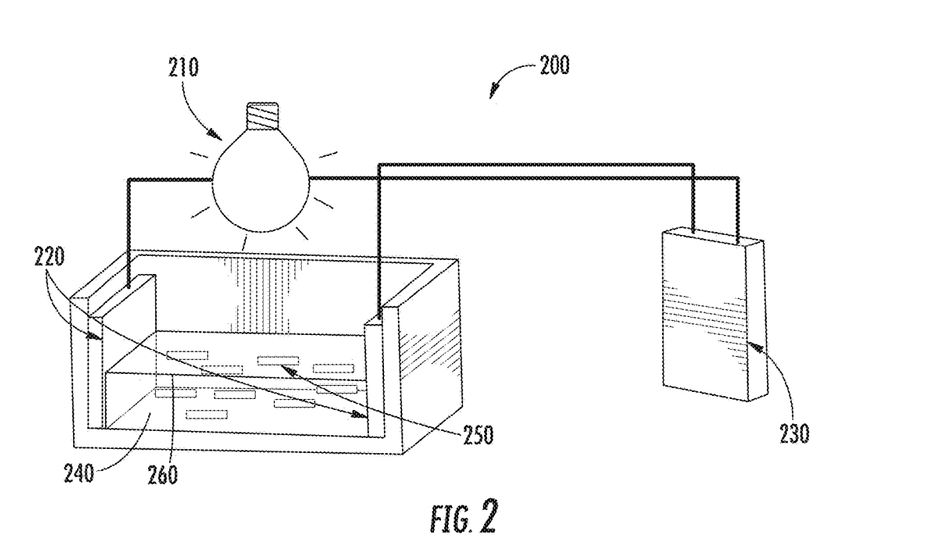
FIG. 2 is a schematic of one embodiment of an apparatus for fiber alignment.

Two parallel metal electrodes were attached to a glass substrate to form a fabricating tank, as shown at FIG. 2. The apparatus 200 of FIG. 2 included a UV lamp 210 and two electrodes 220 that were powered by a power supply 230. The two electrodes 220 flanked a fabricating tank 240 that included fibers 250 and a liquid 260.

The electrodes were tied and bound to the glass substrate by double-sided glue tape, which was believed to substantially prevent unwanted reactions between the metal electrodes and the liquid. The metal electrodes included a copper electrode and a zinc electrode.

The setup was sealed airtight, which was believed to keep the crevices free of liquid during the experiment.

Based on theoretical calculations (see Example 2), larger electric fields improved the resulting alignment. One series circuit of this example consisted of four 12V Pb-batteries, one digital power supply (30V), and one analog power supply (30V), which were connected in series to provide a 108V power supply. Although the 108 V power supply slightly exceeded the power supply needed according to the theoretical calculations of Example 2, it was believed that a slightly higher power supply would compensate for one or more uncertainties, including, but not limited to, the geometry of the fibers, the viscosity of the liquid, etc.

In this example, polymer precursors that included 0.5 wt % chopped fiber, and 1.0 wt % chopped fiber were exposed to an electric field. A polymer precursor, specifically an epoxy resin, was selected as the liquid resin so that, upon curing, a composite material was formed, with the chopped carbon fibers as a reinforcement material for the composite materials.

During the experiments, an electrode sink was placed under an optical microscope for real time observation.

The distance between the two electrodes was 1.35 mm to 2.2 mm, and the average distance between the electrodes was 2 mm.

Before applying the electric field, substantially all of the chopped carbon fibers were substantially evenly dispersed, but randomly oriented, by mechanical stirring and supersonic vibrational homogenization.

Figure 3A:
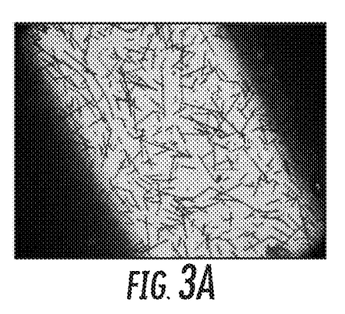
FIG. 3A depicts one embodiment of fibers disposed in a liquid prior to being exposed to an electric field.
Figure 3B:
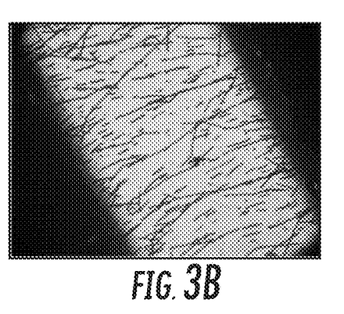
FIG. 3B depicts one embodiment of fibers after being exposed to an electric field for 15 seconds.
Figure 3C:
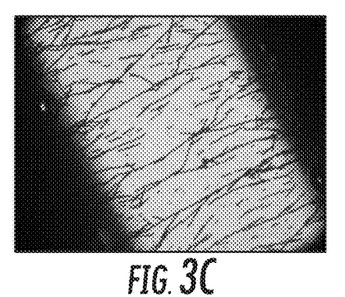
FIG. 3C depicts one embodiment of fibers after being exposed to an electric field for 30 seconds.
Figure 3D:
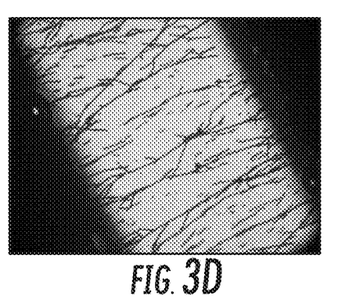
FIG. 3D depicts one embodiment of fibers after being exposed to an electric field for 1 minute.
Figure 3E:
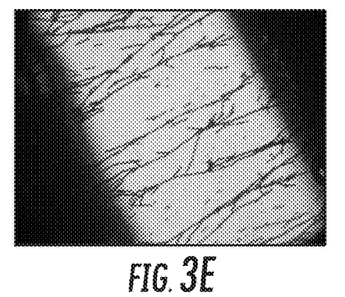
FIG. 3E depicts one embodiment of fibers after being exposed to an electric field for 5 minutes.
Figure 3F:
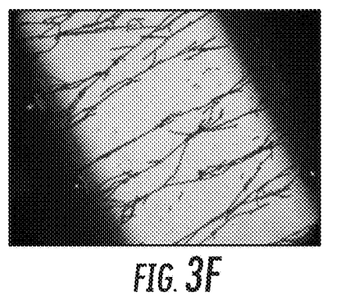
FIG. 3F depicts one embodiment of fibers after being exposed to an electric field for 10 minutes.
Figure 3G:
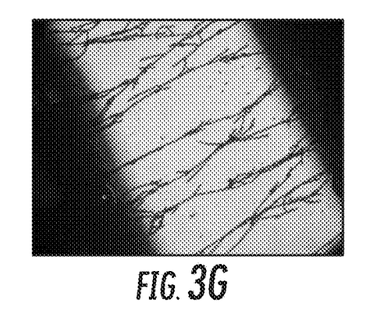
FIG. 3G depicts one embodiment of fibers after being exposed to an electric field for 12 minutes.

Images of the alignment process were collected at 0 seconds (FIG. 3A), 15 seconds (FIG. 3B), 30 seconds (FIG. 3C), 1 minute (FIG. 3D), 5 minutes (FIG. 3E), 10 minutes (FIG. 3F), and 12 minutes (FIG. 3G).

After the DC field was introduced, the chopped fibers started to rotate. The electric force caused substantially all of the carbon fibers to align to a direction parallel to the electric field (perpendicular to the electrodes plane). After 15 seconds, the alignment of a portion of the fibers was observed, and the alignment was substantially complete within 12 minutes.

The experiment proved the influential function of the electric field in aligning neutral polarizable molecules in a liquid environment. When the fibers of this example were exposed to an electric field for longer than 12 minutes, a concatenation phenomenon was observed.

Example 2—Theoretical Derivation on Alignment

In order to determine the parameters of an electric field needed to align certain fibers, a series of theoretical calculations was performed.

Figure 4:
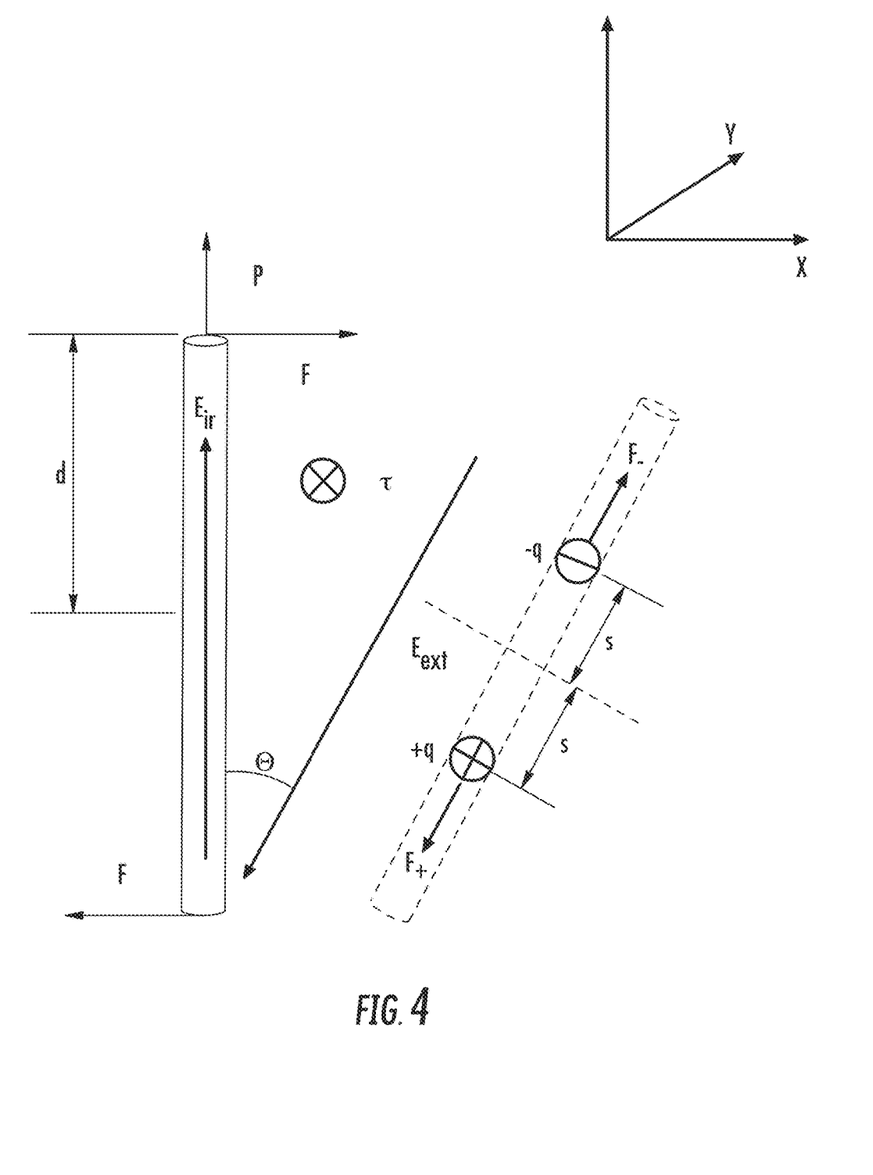
FIG. 4 is a schematic depicting one embodiment of a carbon fiber in a theoretical electric field.

The calculations were based, in part, on the realization that when a neutral particle is positioned in an electric field, the polarization can respond to the field in the form of an instant torque on the positive and negative charges of its atom. The distributions of electrons are moved by external field. Such a process is depicted at FIG. 4. The physical quantity used to describe polarization was polarizability.

The polarizability α, usually a three-dimensional tensor, was understood to correlate electric field and induced dipole moment $\vec{p}$:

$$\vec{p} = \alpha \vec{E} \quad (1)$$

Regarding dielectric spheres in a non-uniform field, it has been shown that the induced dipole of a neutral particle can be determined as follows:

$$p = 4\pi a^3 \varepsilon_0 \kappa_1 \left( \frac{\kappa_2 - \kappa_1}{\kappa_2 + 2\kappa_1} \right) E \quad (2)$$

where a is the radius of the sphere. $\varepsilon_0$ is the dielectric constant of vacuum and is equal to $8.85 \times 10^{-12}$ F/m, $\kappa_1$ is the dielectric constant of liquid resin, $\kappa_2$ is the dielectric constant of the fiber.

Taking a chopped carbon fiber as an example, due to an opposite direction of inner electric field $E_{inn}$, the total electric field across the fiber was theoretically calculated to be—

$$E = E_{ext} - E_{inn} \quad (3)$$

Therefore, in embodiments, the work needed to align the fibers was believed to include two parts: 1) producing the dipole; and 2) aligning the dipole along the direction of electric field.

(1) Producing the Dipole

To evaluate the work to produce the dipole, it was necessary to introduce a pair of forces, $F_+$ and $F_-$, acting on two opposite ends of fiber during the process of polarization. It was assumed that the charge of the entire fiber was 2q and the length of the fiber was 2d. The force pair exerting at a distance of s from the center was represented as—

$$F_\pm = \frac{s}{d} qE \quad (4)$$

In order to pull all the electric charges to the ends of the fiber and integrate the force along d, the following was determined:

$$W_1 = \int_0^d F_\pm ds = \frac{qE}{d} \int_0^d s \, ds = \frac{1}{2} qEd = \frac{1}{2} pE \quad (5)$$

(2) Aligning the Dipole Along the Direction of Electric Field

The second part of work concerned the torque exerted on fibers and the angle fibers rotate. Specifically, as explained at Example 1, the fiber, under the impact of electric force at the beginning of the process, was believed to rotate to the position depicted at FIG. 4 (shown as dashed lines). According to the definition, in a three-dimensional space, the torque equaled the cross-product of moment and force:

$$\tau = \vec{p} \times \vec{E} = pE \sin \theta \quad (6)$$

It was assumed that the initial position of a carbon fiber in an electric field was at an arbitrary angle θ, and by integrating torque with respect to angular increment, the result would be—

$$W_2 = \int_\theta^0 \tau(\theta) d\theta = -pE\cos\theta \big|_\theta^0 = -pE + pE\cos\theta = U(0) - U(\theta) \quad (7)$$

where U(θ) was the electric potential, according to the following definition:

$$U(\theta) = -pE \cos \theta \quad (8)$$

In extreme cases, when all the fibers initially were perpendicular to the electric field, the maximum work to align all carbon fibers when the initial angle θ was selected as $$\frac{\pi}{2}.$$

(3) All Work Required for Carbon Fiber (as an Example)

Adding $W_1$ and $W_2$, and after substitution $$\theta = \frac{\pi}{2},$$

the final expression of work needed to be done to realize alignment, in certain embodiments, was—

$$W = W_1 + W_2 = -pE + pE\cos\left(\frac{\pi}{2}\right) + \frac{1}{2}pE = -\frac{1}{2}pE \quad (9)$$

Thus, the static mechanical analysis of carbon fiber subjected to electric field was completed.

A concise and accurate method was proposed by Pohl (H. A. Pohl, Dielectrophoresis: the behavior of neutral matter in nonuniform electric fields, Cambridge Univ. Press, 1978), who provided the expression of local electric field inside the neutral particle as—

$$E_{inn} = \frac{3\varepsilon_1}{\varepsilon_2 + 2\varepsilon_1} E_{ext} \quad (10)$$

Then subtracted was the local electric field with external field in equation (3):

$$E = \frac{\varepsilon_2 - \varepsilon_1}{\varepsilon_2 + 2\varepsilon_1} E_{ext} \quad (11)$$

Combining equations (2), (9) and (11), the final work needed to align carbon fiber under required electric field strength, in certain embodiments, was calculated to be—

$$W = -2\pi a^3 \varepsilon_0 \kappa_1 \left(\frac{\kappa_2 - \kappa_1}{\kappa_2 + 2\kappa_1} E\right)^2 \quad (12)$$

where a was the radius of spherical particle. With regard to carbon fiber, a was replaced by the fiber's radius of gyration:

$$a = ((R^2/2) + (l^2/12))^{1/2} \approx (l^2/12)^{1/2} \quad (13)$$

A sinusoidal electric field was applied, therefore, the scalar value of electric field was calculated to be—

$$E^2 = \frac{\int_0^T (A\sin(\omega t))^2 dt}{\int_0^T dt} = \frac{A^2}{2} \quad (14)$$

where A was the amplitude of sinusoidal electric field strength. When applied into equation (12), the following was obtained:

$$W = -\pi(l^2/12)^{3/2} \varepsilon_0 \kappa_1 \left(\frac{\kappa_2 - \kappa_1}{\kappa_2 + 2\kappa_1} A\right)^2 \quad (15)$$

Then when the dimension of a carbon fiber and relative electric constants (effective dielectric constant, conductivity etc.) were known, by employing estimation equation (11) and equation (12), the required electric work W was able to be calculated for certain embodiments.

Based on T. B. Jones, Electromechanics of Particles, Cambridge Univ. Press, Cambridge, 1995, the required electric field used to align carbon fibers may be larger than a value as—

$$|W| \geq K_B T \quad (16)$$

where $K_B$ is Boltzmann's constant ($1.38 \times 10^{-23}$ JK$^{-1}$), T is absolute temperature (K).

Conclusion on Theoretical Derivation of Minimum Required Electric Field

By comparing equation (15) with equation (16), the required electric field strength for certain embodiments was calculated. In this example, the length of carbon fiber 1 was assumed to be 0.15 mm (in average), and the radius of carbon fiber was 8 μm. The dielectric constant was chosen as $\kappa_1 = 2.85$. The dielectric constant of liquid resin (polymer precursor in this research) was $\kappa_2 = 3.45$. The vacuum permittivity $\varepsilon_0$ was taken as $8.85 \times 10^{-12}$ F/m. The experimental temperature was controlled around 160° C. (433K).

The parameters used in the calculations are shown in the following table:

TABLE 1

| Parameters Used in Calculations of Example 2 | | |
|---|---|---|
| | Value | Unit |
| Average Length of Carbon Fibers | 150 | μm |
| Average Radius of Carbon Fibers | 8 | μm |
| Dielectric Constant of Carbon Fiber | 3.495 | |
| Dielectric Constant of Precursor | 3.502 | |
| Experiment Temperature | 433 | K |
| Vacuum Permittivity | $8.85 \times 10^{-12}$ | F/m |
| Boltzmann's Constant | $1.38 \times 10^{-23}$ | JK$^{-1}$ |
| Viscosity | 0.1 | Pa · s |

Using the liquid resin, the value of required electric field was at least 46.6V/mm, according to the foregoing calculations. It was observed that the larger the aspect ratio of carbon fiber was assumed to be, theoretically a smaller electric field was needed to align the carbon fiber.

When it was assumed that the tank of Example 1 (see FIG. 2) was 2 mm in length (which was the distance between the two electrodes), the total required power supply for alignment was 93.2 volts, regardless of the width and depth of the tank, and the volume fraction of fibers in the solution. All judging conditions were based on the fact that the summation of electric potential and the energy used to induce molecular dipole should complete thermal agitations.

Example 3—Calculation of Required Electric Fields

The electric fields required to form a 12 inch×12 inch mat-shaped composite material comprising substantially aligned chopped carbon fibers of different lengths and diameter and at different fabrication temperatures were calculated. The fabrication temperature played an important role in the calculations, because of its supposed effect on alignment of the fibers. It was believed that at lower fabrication temperatures, less electric field intensity was required to at least substantially align the fibers. In theory, at a fabrication temperature of absolute zero, a very small electric field would be required to align chopped fibers.

The minimum electric fields for fibers having a length of 2 μm, 10 μm, 100 μm, 1 mm, 10 mm, and 50 mm, and a diameter of 0.1 μm and 1 μm, at fabrication temperatures of 10 K, 298.15 K, 373.15 K, and 473.15 K are shown in the following table:

TABLE 2

| | | Required Electric Fields (Calculated) | | | | | | | |
|---|---|---|---|---|---|---|---|---|---|
| | | Fabrication Temperature (10 K) Fiber Diameter | | Fabrication temperature (25° C. = 298.15 K) Fiber Diameter | | Fabrication temperature (100° C. = 373.15 K) Fiber Diameter | | Fabrication temperature (200° C. = 473.15 K) Fiber Diameter | |
| Required Electric field (V) | | 0.1 μm | 1 μm | 0.1 μm | 1 μm | 0.1 μm | 1 μm | 0.1 μm | 1 μm |
| Fiber Length | 2 μm | $2.248 \times 10^5$ | $1.143 \times 10^5$ | $6.701 \times 10^6$ | $3.408 \times 10^6$ | $8.388 \times 10^6$ | $4.265 \times 10^6$ | $1.064 \times 10^7$ | $5.408 \times 10^6$ |
| | 10 μm | $2.032 \times 10^4$ | $1.946 \times 10^4$ | $6.058 \times 10^5$ | $5.802 \times 10^5$ | $7.582 \times 10^5$ | $7.261 \times 10^5$ | $9.614 \times 10^5$ | $9.207 \times 10^5$ |
| | 100 μm | $6.430 \times 10^2$ | $6.430 \times 10^2$ | $1.917 \times 10^4$ | $1.916 \times 10^4$ | $2.399 \times 10^4$ | $2.399 \times 10^4$ | $3.042 \times 10^4$ | $3.042 \times 10^4$ |
| | 1 mm | 20.329 | 20.329 | 606.105 | 606.102 | 758.577 | 758.577 | 961.867 | 961.867 |
| | 10 mm | 0.643 | 0.643 | 19.167 | 19.167 | 23.994 | 23.994 | 30.424 | 30.424 |
| | 50 mm | 0.058 | 0.058 | 1.714 | 1.714 | 2.164 | 2.164 | 2.744 | 2.744 |

The Required Electric Fields of Table 2 are minimum electric fields that may be exceeded, as described herein.

I claim:

1. A method of aligning fibers, the method comprising:
providing one or more fibers of a dielectric material disposed in a non-solvent liquid, wherein the one or more fibers are completely submerged in the non-solvent liquid; and
exposing the one or more fibers to an electric field for a time sufficient to at least substantially align at least a portion of the one or more fibers in the non-solvent liquid;
wherein the non-solvent liquid comprises a polymer precursor, the one or more fibers are present in the non-solvent liquid in an amount of about 1 to about 20 weight percent, based on the combined weight of the one or more fibers and the non-solvent liquid, and the one or more fibers comprise macroscale fibers, microscale fibers, or a combination thereof.

2. The method of claim 1, wherein the polymer precursor is an epoxy resin.

3. The method of claim 1, further comprising curing the polymer precursor to form a composite material.

4. The method of claim 1, wherein the one or more fibers comprise carbon, Si, $SiO_2$, SiC, $Si_3N_4$, $Al_2O_3$, or a combination thereof.

5. The method of claim 1, wherein the one or more fibers comprise carbon fibers, carbon nanofibers, single wall carbon nanotubes, multi-wall carbon nanotubes, or a combination thereof.

6. The method of claim 1, wherein the electric field is provided by at least two electrodes connected to a power supply.

7. The method of claim 6, wherein the at least two electrodes are metal electrodes.

8. The method of claim 7, wherein the metal electrodes comprise zinc electrodes and/or copper electrodes.

9. The method of claim 6, wherein the at least two electrodes are arranged at an average distance from each other of about 1.3 mm to about 2.2 mm.

10. The method of claim 1, wherein the time is about 1 second to about 20 minutes.

11. The method of claim 1, wherein the time is about 15 seconds to about 12 minutes.

12. The method of claim 1, wherein the one or more fibers are substantially evenly dispersed in the non-solvent liquid.

13. A composite material comprising one or more fibers of a dielectric material aligned by the method of claim 1.

14. The method of claim 1, wherein the one or more fibers and the non-solvent liquid are disposed in a tank, and the exposing of the one or more fibers to the electric field comprises applying the electric field with a first electrode and a second electrode, wherein the tank is arranged between the first electrode and the second electrode, and the first electrode and the second electrode are in contact with the tank.

15. A method of aligning fibers, the method comprising:
providing one or more fibers of a dielectric material disposed in a non-solvent liquid comprising a polymer precursor, wherein the one or more fibers are completely submerged in the non-solvent liquid;
exposing the one or more fibers to an electric field for a time of about 10 seconds to about 15 minutes to at least substantially align at least a portion of the one or more fibers, wherein the electric field is provided by at least two metal electrodes connected to a power supply; and
curing the polymer precursor to form a composite material,
wherein the one or more fibers are present in the non-solvent liquid in an amount of about 1 to about 20 weight percent, based on the combined weight of the one or more fibers and the non-solvent liquid.

16. The method of claim 15, wherein the one or more fibers comprise carbon, and have an average length of about 1 μm to about 200 μm, and an average diameter of about 0.1 μm to about 14 μm.

17. The method of claim 15, wherein the one or more fibers comprise carbon, and have an average length of about 1 mm to about 100 mm, and an average diameter of about 0.1 μm to about 14 μm.

18. A method of aligning fibers, the method comprising:
providing fibers of a dielectric material disposed in a non-solvent liquid, wherein the fibers are completely submerged in the non-solvent liquid; and
exposing the fibers to an electric field for a time effective to substantially align at least a portion of the fibers in the non-solvent liquid;
wherein the non-solvent liquid comprises a polymer precursor, and the fibers are present in the non-solvent liquid in an amount of about 5 to about 20 weight percent, based on the combined weight of the fibers and the non-solvent liquid.

19. The method of claim 18, wherein the fibers comprise carbon, Si, $SiO_2$, SiC, $Si_3N_4$, $Al_2O_3$, or a combination thereof.

20. The method of claim 18, wherein the fibers comprise carbon fibers, carbon nanofibers, single wall carbon nanotubes, multi-wall carbon nanotubes, or a combination thereof.

* * * * *